(12) United States Patent
Howland

(10) Patent No.: US 6,836,139 B2
(45) Date of Patent: Dec. 28, 2004

(54) METHOD AND APPARATUS FOR DETERMINING DEFECT AND IMPURITY CONCENTRATION IN SEMICONDUCTING MATERIAL OF A SEMICONDUCTOR WAFER

(75) Inventor: William H. Howland, Wexford, PA (US)

(73) Assignee: Solid State Measurments, Inc., Pittsburgh, PA (US)

( * ) Notice: Subject to any disclaimer, the term of this patent is extended or adjusted under 35 U.S.C. 154(b) by 227 days.

(21) Appl. No.: 10/277,689

(22) Filed: Oct. 22, 2002

(65) Prior Publication Data

US 2004/0075460 A1 Apr. 22, 2004

(51) Int. Cl.[7] ............................................... G01R 31/26
(52) U.S. Cl. .................................... 324/766; 324/158.1
(58) Field of Search ................................. 324/766, 765, 324/158.1, 752, 751, 753; 73/105; 250/307, 306

(56) References Cited

U.S. PATENT DOCUMENTS

| | | | |
|---|---|---|---|
| 4,168,212 A | 9/1979 | Faktor et al. ................. 254/1 T |
| 4,581,578 A | 4/1986 | Honma et al. ............ 324/158 D |
| 5,065,103 A | * 11/1991 | Slinkman et al. ............ 324/458 |
| 5,406,214 A | 4/1995 | Boda et al. ................... 324/765 |
| 5,453,703 A | 9/1995 | Goldfarb ....................... 324/765 |
| 5,477,158 A | 12/1995 | Shafer et al. ................. 324/753 |
| 5,663,657 A | 9/1997 | Lagowski et al. ........... 324/766 |
| 5,977,788 A | 11/1999 | Lagowski .................... 324/765 |
| 6,011,404 A | 1/2000 | Ma et al. ...................... 324/765 |
| 6,150,175 A | 11/2000 | Shelton et al. ................. 436/80 |
| 6,185,991 B1 | * 2/2001 | Hong et al. .................... 73/105 |
| 6,197,606 B1 | 3/2001 | Polignano et al. ............. 438/17 |
| 6,211,686 B1 | * 4/2001 | Matsuzawa et al. ......... 324/719 |
| 6,211,961 B1 | 4/2001 | Maris .......................... 356/432 |
| 6,275,060 B1 | 8/2001 | Ahrenkiel et al. ........... 324/766 |
| 6,297,659 B1 | 10/2001 | Saito ........................... 324/765 |
| 6,315,574 B1 | 11/2001 | Kamieniecki et al. ......... 439/16 |
| 6,340,642 B1 | 1/2002 | Arndt et al. ................. 438/780 |
| 6,346,821 B1 | 2/2002 | Baumgart .................... 324/766 |
| 6,369,603 B1 | 4/2002 | Johnston et al. ............ 324/766 |
| 6,426,644 B1 | 7/2002 | Borden et al. .............. 324/765 |
| 2002/0006740 A1 | 1/2002 | Kamieniecki et al. ...... 438/795 |

* cited by examiner

Primary Examiner—David Zarneke
Assistant Examiner—Tung X. Nguyen
(74) Attorney, Agent, or Firm—Webb Ziesenheim Logsdon Orkin & Hanson, P.C.

(57) ABSTRACT

A charge carrier lifetime of a semiconductor wafer is measured by contacting an electrically conductive measurement probe to a surface of a semiconductor wafer to form a capacitor. A DC voltage having an AC voltage superimposed thereon is applied to the capacitor and the DC voltage is swept between a first voltage and a second voltage. At the second voltage, the semiconductor wafer adjacent the contact between the measurement probe and the surface of the semiconductor wafer is exposed to a light pulse. After the light pulse terminates, a change in the capacitance of the capacitor over time is determined. From the thus determined change in capacitance, a charge carrier lifetime of the semiconductor wafer is determined.

20 Claims, 4 Drawing Sheets

METHOD AND APPARATUS FOR DETERMINING DEFECT AND IMPURITY CONCENTRATION IN SEMICONDUCTING MATERIAL OF A SEMICONDUCTOR WAFER

BACKGROUND OF THE INVENTION

1. Field of the Invention

The present invention relates to charge carrier lifetime measurement of product semiconductor wafers.

2. Description of Related Art

It is well known in the art of semiconductor wafer processing that defects and impurities in the semiconducting material of the semiconductor wafer can affect the lifetime of integrated circuits formed from the wafer. Heretofore, however, charge carrier lifetime measurements were typically performed on test semiconductor wafers, not product semiconductor wafers. An obvious problem with performing charge carrier lifetime measurements on test wafers is that there may not be a sufficient correlation between the charge carrier lifetime measurement of a test wafer and the charge carrier lifetime of one or more corresponding product wafers.

It is, therefore, an object of the present invention to overcome the above problem and others by providing a method and apparatus for non-destructively determining a charge carrier lifetime of a product semiconductor wafer. Still other objects will occur to others upon reading and understanding the following detailed description.

SUMMARY OF THE INVENTION

The invention is a method of measuring a charge carrier lifetime of a semiconductor wafer that includes contacting an electrically conductive measurement probe to a surface of a semiconductor wafer to form a capacitor and applying a DC voltage having an AC voltage superimposed thereon between the measurement probe and the semiconductor wafer. The DC voltage is swept between a first voltage and a second voltage. The semiconductor wafer adjacent the contact between the measurement probe and surface of the semiconductor wafer is exposed to a light pulse. After the light pulse terminates, a change in capacitance of the capacitor over time is determined. From this thus determined change in capacitance, a charge carrier lifetime of the semiconductor wafer is determined.

The semiconductor wafer can include a dielectric overlaying semiconductor material. The measurement probe contacts the dielectric to form the capacitor whereupon the measurement probe defines a first plate of the capacitor, the semiconductor material defines a second plate of the capacitor and the dielectric defines an electrical insulator therebetween.

The measurement probe can include a dielectric that contacts a semiconductor wafer. The use of a measurement probe having dielectric enables formation of the capacitor when the probe is utilized to measure the charge carrier lifetime of a semiconductor wafer not having an overlaying dielectric.

At least the part of the measurement probe that contacts the semiconductor wafer can be formed from an elastically deformable material.

At the second voltage, the capacitor has a minimum capacitance value. In response to the light pulse, the capacitance value increases from the minimum capacitance value. After the light pulse terminates, the capacitance value decreases from the increased capacitance value to the minimum capacitance value.

The step of determining a change in capacitance can include determining a time rate of change in the capacitance of the capacitor. This time rate of change in the capacitance of the capacitor can be utilized to determine the charge carrier lifetime of the semiconductor wafer. The time rate of change in the capacitance of the capacitor is preferably determined temporally adjacent the termination of the light pulse. However, this is not to be construed as limiting the invention.

The exposure of the semiconductor wafer to the light pulse and the determination of the change in capacitance of the capacitor over time preferably occur in the presence of the second voltage. However, this is not to be construed as limiting the invention.

The invention is also a semiconductor wafer charge carrier lifetime measuring apparatus. The apparatus includes an electrically conductive wafer chuck for supporting a backside of a semiconductor wafer and an electrically conductive measurement probe. A movement means is provided for moving the measurement probe and a topside of the semiconductor wafer into contact when the wafer chuck is supporting the semiconductor wafer. The contact between the semiconductor wafer and the measurement probe forms a capacitor. An electrical stimulus means is provided for applying a DC voltage having an AC voltage superimposed thereon to the capacitor and for sweeping the DC voltage from a first voltage to a second voltage. A light source supplies a light pulse to the semiconductor wafer adjacent the contact thereof with the measurement probe. A measurement means is provided for measuring a change in capacitance of the capacitor over time after the light pulse terminates and for determining from the change in capacitance over time a charge carrier lifetime of the semiconductor wafer.

More specifically, the measuring means determines a time rate of change in the capacitance of the capacitor and determines the charge carrier lifetime of the semiconductor wafer from the time rate of change in the capacitance of the capacitor.

Lastly, the invention is a method of measuring a charge carrier lifetime of a semiconductor wafer that includes forming a capacitor with a top surface of a semiconductor wafer and sweeping a test voltage applied to the capacitor from a first voltage to a second voltage. A light pulse is applied to the semiconductor wafer whereupon the capacitance of the capacitor increases. A time rate of change in a decay of the capacitance of the capacitor is determined and a charge carrier lifetime of the semiconductor wafer is determined from the thus determined time rate of change in the decay of the capacitance of the capacitor.

BRIEF DESCRIPTION OF THE DRAWINGS

FIG. 1(*b*) is a second embodiment of a semiconductor wafer charge carrier lifetime measuring apparatus;

DETAILED DESCRIPTION OF THE INVENTION

The invention will be described with reference to the accompanying figures where like reference numbers correspond to like elements.

Figure 1:
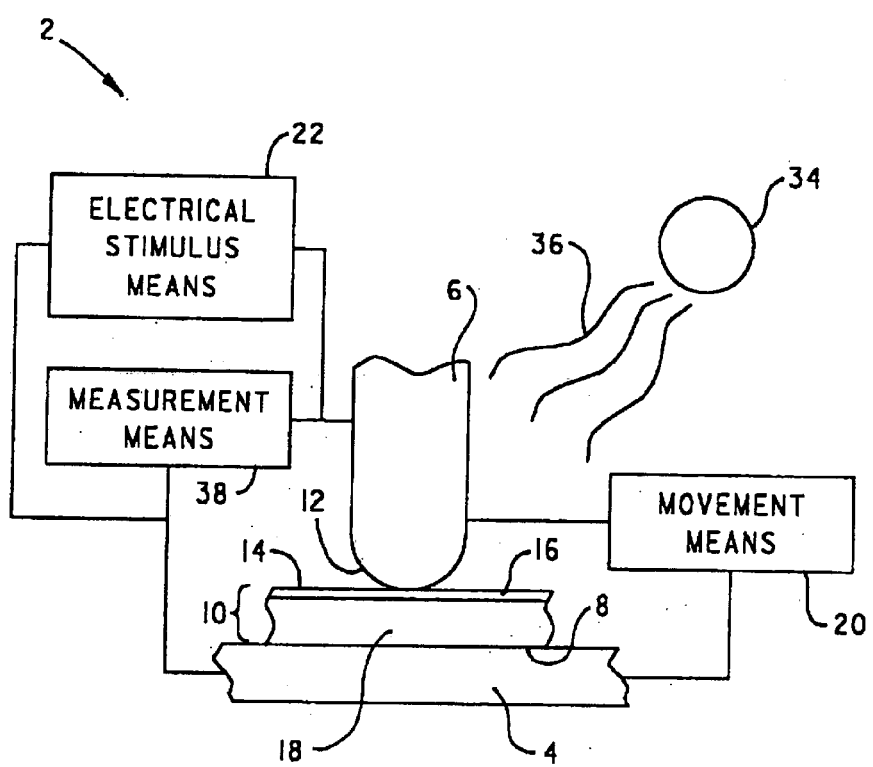
FIG. 1(*a*) is a first embodiment of a semiconductor wafer charge carrier lifetime measuring apparatus.

With reference to FIG. 1(a), a first embodiment apparatus 2 for measuring a semiconductor wafer charge carrier lifetime includes an electrically conductive chuck 4 and an elastically deformable, electrically conductive measurement probe 6. Chuck 4 is configured to support a backside 8 of a semiconductor wafer 10. A distal end 12 of probe 6 has a curved or arcuate surface for contacting a topside 14 of semiconductor wafer 10. However, this is not to be construed as limiting the invention since distal end 12 of probe 6 can have any suitable shape. A movement means 20 can be connected to chuck 4, probe 6 or both for moving distal end 12 of probe 6 and topside 14 of semiconductor wafer 10 into contact.

Figure 2:
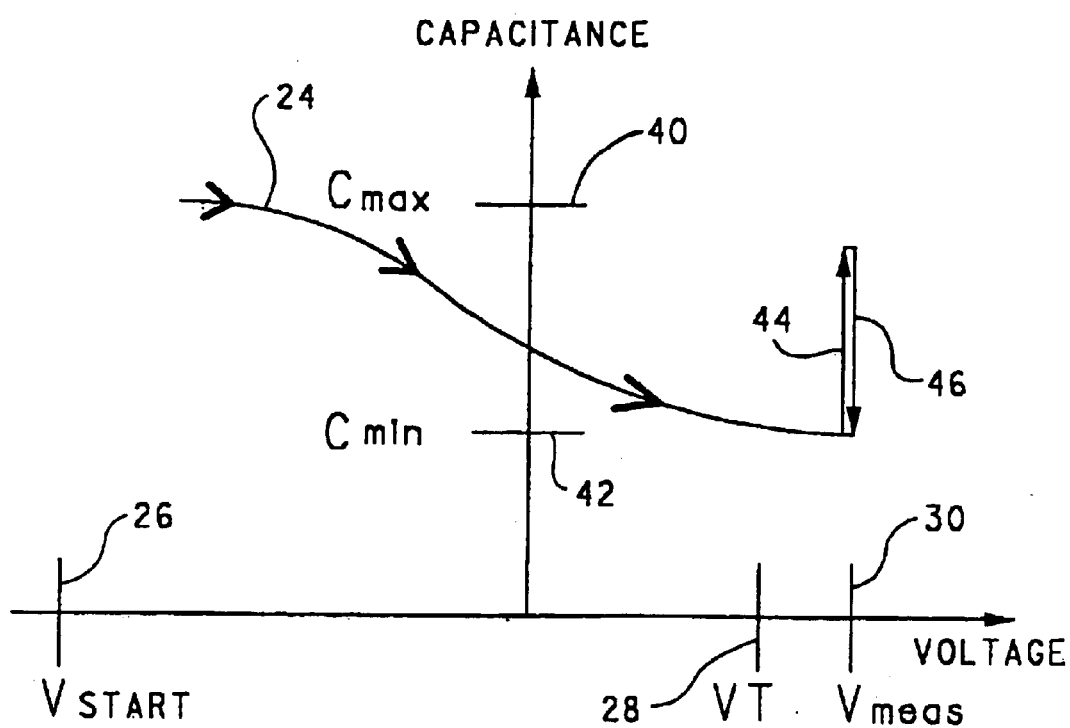
FIG. 2 is a graph of capacitance versus voltage for the capacitor formed by the probe and semiconductor wafer in each of FIGS. 1(*a*) and 1 (*b*) in response to a voltage sweep and a light pulse.

An electrical stimulus means 22 is electrically connected between chuck 4 and probe 6 for applying a suitable test stimulus to semiconductor wafer 10 when it is received on chuck 4 and distal end 12 of probe 6 is in contact with topside 14 of semiconductor wafer 10. One suitable test stimulus is a CV-type electrical stimulus 24 of the type shown in FIG. 2 wherein a DC voltage 24 having an AC voltage (not shown) superimposed thereon is swept from a first voltage ($V_{START}$) 26, which is less than a threshold voltage ($V_T$) 28 of semiconductor wafer 10, to a second voltage ($V_{MEAS}$) 30 which is greater than threshold voltage 28. The DC voltage is swept slowly enough to allow for minority carrier generation in the semiconductor material underlying the contact between probe 6 and semiconductor wafer 10. CV-type electrical stimulus 24 is for semiconductor wafer 10 formed from p-type silicon. A mirror-image of CV-type electrical stimulus 24 would be utilized for semiconductor wafer 10 formed from n-type silicon.

Apparatus 2 includes a light source 34, such as a xenon lamp, which can be positioned to direct a light pulse 36 toward semiconductor wafer 10 adjacent the contact with probe 6. A measurement means 38 is connected between chuck 4 and probe 6 for measuring a response of semiconductor wafer 10 to light pulse 36 and for determining from this measurement a charge carrier lifetime of semiconductor wafer 10.

In the embodiment shown in FIG. 1(a), semiconductor wafer 10 includes a dielectric 16 overlaying semiconductor material 18. Thus, in this embodiment, topside 14 of semiconductor wafer 10 is the side of dielectric 16 opposite semiconductor material 18.

Figure 1B:
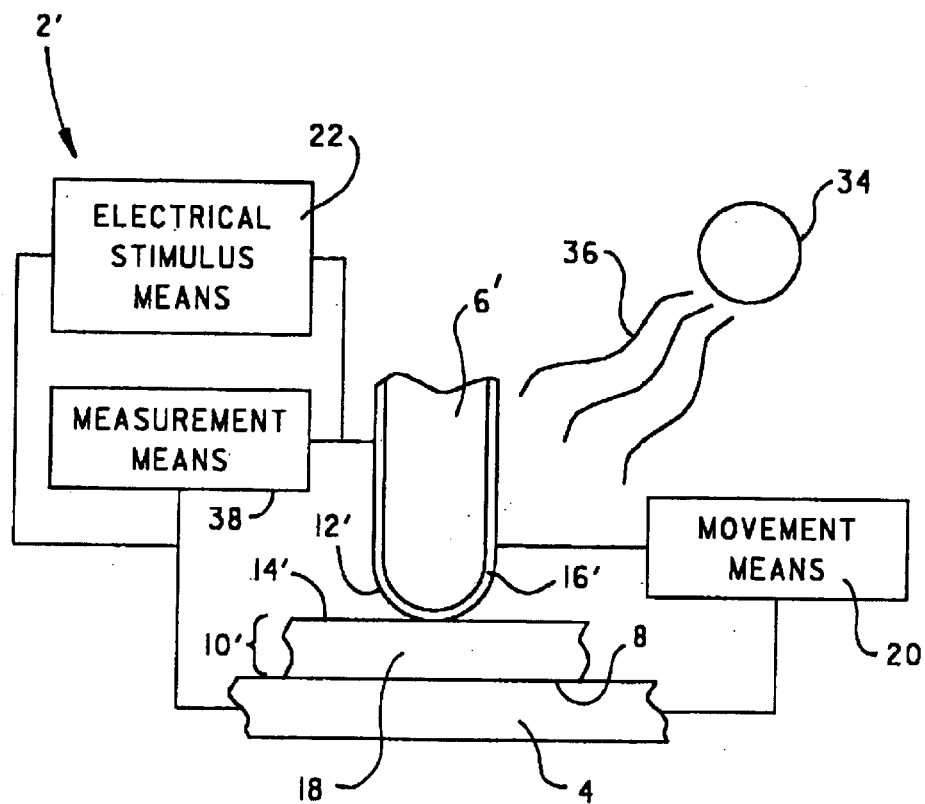

With reference to FIG. 1(b), and with continuing reference to FIG. 1(a), a second embodiment apparatus 2' for measuring a charge carrier lifetime of a semiconductor wafer includes electrically deformable, electrically conductive probe 6' having a dielectric 16' covering at least its distal end 12'. The addition of dielectric 16' on electrically conductive probe 6' enables electrical measurements to be made directly on semiconductor material 18 of semiconductor wafer 10'. In other words, where semiconductor wafer 10' does not include dielectric overlaying semiconductor material 18, probe 6' having dielectric 16' over distal end 12' can contact top surface 14' of semiconductor material 18 directly.

Probes 6 and 6' can be formed from any suitable material that is elastically deformable and electrically conductive.

One suitable material is tantalum. To this end, at least distal end 12 of probe 6 is formed from tantalum and includes on its outer surface a native oxide layer that grows thereon in response to exposure to atmosphere. In contrast, probe 6' is a tantalum probe and dielectric 16' is a thermally grown metallic oxide. However, dielectric 16' can be any suitable material having a high dielectric constant that can be grown or applied to the exterior surface of probe 6' adjacent at least its distal end 12'. Suitable materials include those having dielectric constants greater than 3.9. One example of a grown dielectric is tantalum oxide. One example of an applied dielectric 16' is silicon rubber. However, these examples are not to be construed as limiting the invention since the use of any suitable grown or applied dielectric 16' is envisioned.

In the first embodiment of apparatus 2, shown in FIG. 1(a), contact between distal end 12 of probe 6 and top surface 14 of semiconductor wafer 10 forms a capacitor. More specifically, probe 6 defines a first plate of the capacitor, semiconductor material 18 defines a second plate of the capacitor and dielectric 16 defines an electrical insulator therebetween. Similarly, in the second embodiment apparatus 2', shown in FIG. 1(b), contact between distal end 12' of probe 6' and topside 14' of semiconductor wafer 10' forms a capacitor. In this latter embodiment, the electrically conductive portion of probe 6' defines a first plate of the capacitor, semiconductor material 18 defines a second plate of the capacitor and dielectric 16' defines the electrical insulator therebetween.

In a method of using apparatus 2 shown in FIG. 1(a), backside 8 of semiconductor wafer 10 is supported by chuck 4, and distal end 12 of probe 6 and topside 14 of semiconductor wafer 10 are moved into contact. Thereafter, electrical stimulus means 22 applies CV-type electrical stimulus 24 between probe 6 and chuck 4. More specifically, electrical stimulus means 22 sweeps a DC voltage having an AC voltage superimposed thereon between first voltage 26 and second voltage 30. During application of CV-type electrical stimulus 24, measurement means 38 observes a change in the capacitance of the capacitor formed by probe 6 and semiconductor wafer 10 from a maximum capacitance ($C_{max}$) 40 at first voltage 26 to a minimum capacitance ($C_{min}$) 42 at second voltage 30.

When CV-type electrical stimulus is at second voltage 30, light source 34 is caused to output light pulse 36. The light from light pulse 36 is absorbed in semiconductor material 18 just under the contact point with probe 6. This absorption takes place through the photo-generation of electron-hole pairs which increase the capacitance of the capacitor formed by probe 6 and semiconductor wafer 10. Preferably, the intensity of light pulse 36 is sufficient enough that the capacitance measured by measurement means 38 reaches maximum capacitance 40. However, this is not be construed as limiting the invention. This increase in capacitance is shown by arrow 44 in FIG. 2. Upon termination of light pulse 36, the capacitance of the capacitor formed by probe 6 and semiconductor wafer 10 decreases from maximum capacitance 40 to minimum capacitance 42 as shown by arrow 46 in FIG. 2.

Figure 3:
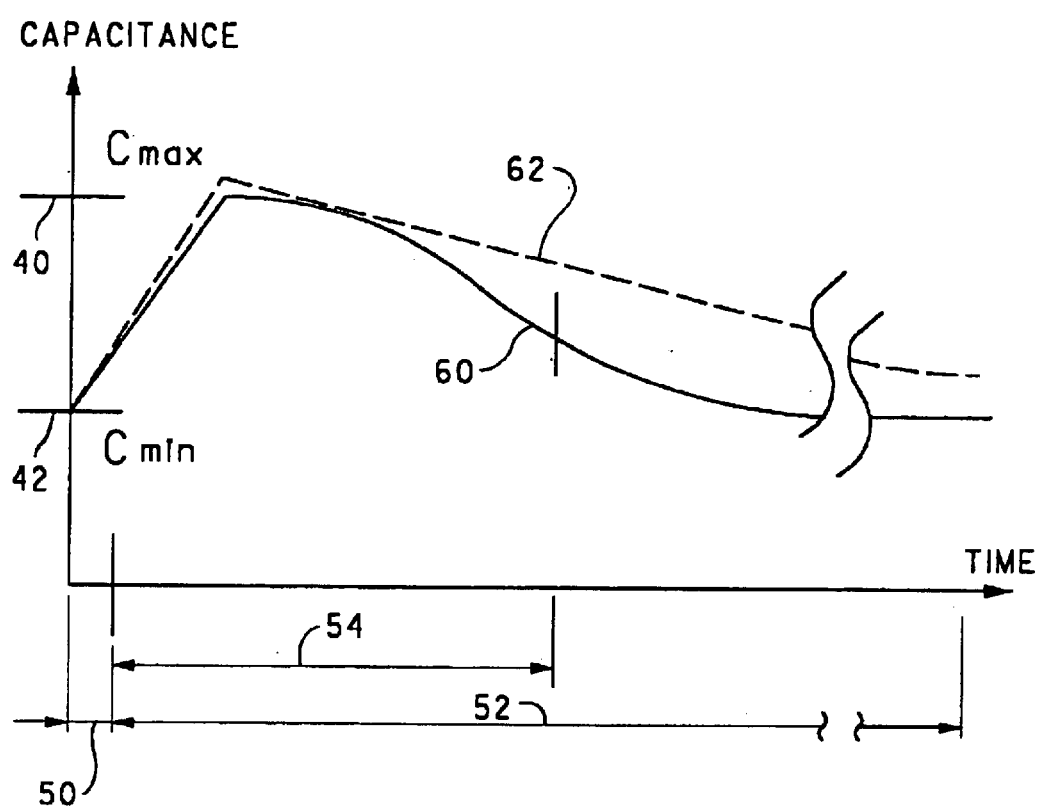
FIG. 3 is a graph of capacitance versus time for the capacitor formed by the probe and semiconductor wafer in each of FIGS. 1(a) and 1(b) in response to the voltage sweep and the light pulse.

With reference to FIG. 3 and with continuing reference to all previous figures, the capacitance of the capacitor formed by probe 6 and semiconductor wafer 10 increases from minimum capacitance 42 to maximum capacitance 40 during a time interval 50 of light pulse 36. At the end of interval 50, light pulse 36 terminates and electron-hole pairs generated in response to interaction between light pulse 36 and semiconductor material 18 of semiconductor wafer 10 commence recombination whereupon the capacitance of the capacitor formed by probe 6 and semiconductor wafer 10 commences decreasing from maximum capacitance 40 to minimum capacitance 42 over a time interval 52. The rate of this recombination and, hence, the decrease in capacitance depends highly on the defect and impurity concentration of semiconductor material 18. Measurement means 38 determines the change in capacitance of the capacitor over time and determines therefrom a charge carrier lifetime of semiconductor wafer 10. More specifically, measurement means 38 determines a time rate of change in the capacitance of the capacitor and determines from this time rate of change the charge carrier lifetime of semiconductor wafer 10.

Since the rate of recombination of photo-generated electron-hole pairs is greatest shortly after light pulse 36 terminates, the time rate of change of the capacitance of the capacitor is determined temporally adjacent the termination of light pulse 36. To this end, the time rate of change in the capacitance of the capacitor is determined at the end of a time interval 54 after termination of light pulse 36.

The time rate of change of the capacitance of the capacitor at the end of interval 54 can be correlated to the defect and impurity concentration of semiconductor material 18. It is preferable that measurement of the time rate of change in the capacitance of capacitors formed with different semiconductor wafers 10 occurs at approximately the same point in time after termination of light pulse 36 to enable correlation among the semiconductor wafers 10 with regard to defect and impurity concentration in the semiconductor materials thereof. However, this is not to be construed as limiting the invention.

In FIG. 3, a solid line 60 shows a change in capacitance over time for a semiconductor material 18 having a high concentration of impurities and a dashed line 62 shows a change in capacitance over time for a semiconductor material 18 having a low impurity concentration. As can be seen, at the end of interval 54, the time rate of change of line 60 is greater than the time rate of change of line 62. More specifically, line 60, related to semiconductor material 18 having a high impurity concentration, has a greater slope than line 62, related to semiconductor material 18 having a low impurity concentration. The difference in slope between line 62 and line 60 can be correlated to the charge carrier lifetime of two different semiconductor wafers 10.

While the foregoing method has been described with reference to a first embodiment of apparatus 2 shown in FIG. 1(a), it will be apparent to one of ordinary skill in the art that the foregoing method is equally applicable to second embodiment apparatus 2' shown in FIG. 1(b). Accordingly, to avoid needless repetition, a detailed description of the foregoing method in connection with second embodiment apparatus 2' shown in FIG. 1(b) has not been included herein.

As can be seen, the present invention provides a method and apparatus for determining a charge carrier lifetime of a semiconductor wafer. Because the apparatus and method of the present invention is non-destructive, it can be utilized in connection with product semiconductor wafers.

The invention has been described with reference to the preferred embodiments. Obvious modifications and alterations will occur to others upon reading and understanding the preceding detailed description. For example, while the invention has been described with reference to CV-type electrical stimulus 24 for semiconductor wafer 10 formed from p-type silicon, it is to be appreciated that a mirror-image of CV-type electrical stimulus 24 can be utilized for semiconductor wafer 10 formed from n-type silicon. It is intended that the invention be construed as including all such modifications and alterations insofar as they come within the scope of the appended claims or the equivalents thereof.

The invention claimed is:

1. A method of measuring a charge carrier lifetime of a semiconductor wafer comprising:
   (a) contacting an electrically conductive measurement probe to a surface of a semiconductor wafer to form a capacitor;
   (b) applying a DC voltage having an AC voltage superimposed thereon between the measurement probe and the semiconductor wafer;
   (c) sweeping the DC voltage between a first voltage and a second voltage;
   (d) exposing the semiconductor wafer adjacent the contact between the measurement probe and the surface of the semiconductor wafer to a light pulse;
   (e) after the light pulse terminates, determining a change in capacitance of the capacitor over time; and
   (f) determining from the change in capacitance of the capacitor over time, a charge carrier lifetime of the semiconductor wafer.

2. The method of claim 1, wherein:
   the semiconductor wafer includes dielectric overlaying semiconductor material; and
   the measurement probe contacts the dielectric to form the capacitor whereupon the measurement probe defines a first plate of the capacitor, the semiconductor material defines a second plate of the capacitor and the dielectric defines an electrical insulator therebetween.

3. The method of claim 1, wherein:
   the measurement probe includes a dielectric that contacts the semiconductor wafer; and
   the dielectric is one of a grown and applied on an exterior surface of the probe.

4. The method of claim 1, wherein at least the part of the measurement probe that contacts the semiconductor wafer is formed from an elastically deformable material.

5. The method of claim 1, wherein:
   the capacitor has a minimum capacitance value at the second voltage;
   in response to the light pulse, the capacitance value increases from the minimum capacitance value; and
   after the light pulse terminates, the capacitance value decreases from the increased capacitance value to the minimum capacitance value.

6. The method of claim 1, wherein:
   step (e) includes determining a time rate of change in the capacitance of the capacitor; and
   step (f) includes determining from the time rate of change in the capacitance of the capacitor the charge carrier lifetime of the semiconductor wafer.

7. The method of claim 6, wherein the time rate of change in the capacitance of the capacitor is determined temporally adjacent the termination of the light pulse.

8. The method of claim 1, wherein steps (d) and (e) occur in the presence of the second voltage.

9. A semiconductor wafer charge carrier lifetime measuring apparatus comprising:
   an electrically conductive wafer chuck for supporting a backside of a semiconductor wafer;
   an electrically conductive measurement probe;

means for moving the electrically conductive measurement probe and a topside of the semiconductor wafer into contact when the wafer chuck is supporting the semiconductor wafer, the contact between the semiconductor wafer and the probe forming a capacitor;

means for applying a DC voltage having an AC voltage superimposed thereon to the capacitor and for sweeping the DC voltage from a first voltage to a second voltage;

a light source for applying a light pulse to the semiconductor wafer adjacent the contact thereof with the measurement probe; and means for measuring a change in a capacitance of the capacitor over time after the light pulse terminates and for determining from the change in capacitance over time a charge carrier lifetime of the semiconductor wafer.

10. The apparatus of claim 9, wherein the contact is formed between the measurement probe and a dielectric layer overlaying a semiconductor material of the semiconductor wafer.

11. The apparatus of claim 9, wherein at least the part of the measurement probe contacting the semiconductor wafer is formed from an elastically deformable material.

12. The apparatus of claim 9, wherein:
the measurement probe includes a dielectric that contacts the semiconductor wafer; and the dielectric is one of grown and applied on an exterior surface of the probe.

13. The apparatus of claim 9, wherein:
the capacitor has a minimum capacitance value at the second voltage;
in response to the light pulse, the capacitance value increases; and
the measuring means determines the change in capacitance value from the increased capacitance value to the minimum capacitance value over time.

14. The apparatus of claim 9, wherein the measuring means:
determines a time rate of change in the capacitance of the capacitor; and
determines the charge carrier lifetime of the semiconductor wafer from the time rate of change in the capacitance of the capacitor.

15. The apparatus of claim 9, wherein the light source applies a light pulse and the measuring means measures the change in capacitance over time in the presence of the second voltage.

16. A method of measuring a charge carrier lifetime of a semiconductor wafer comprising:

(a) forming a capacitor with a top surface of a semiconductor wafer;

(b) sweeping a test voltage applied to the capacitor from a first voltage to a second voltage;

(c) applying a light pulse to the semiconductor wafer whereupon the capacitance of the capacitor increases;

(d) determining a time rate of change in a decay of the capacitance of the capacitor; and (e) determining a charge carrier lifetime of the semiconductor wafer from the thus determined time rate of change in the decay of the capacitance of the capacitor.

17. The method of claim 16, wherein step (d) is performed after the light pulse terminates.

18. The method of claim 16, wherein step (a) includes sandwiching a dielectric between an electrically conductive measurement probe and semiconductor material of the semiconductor wafer.

19. The method of claim 18, wherein the dielectric is one of:
a dielectric overlaying the semiconductor material; and
a dielectric one of grown and applied on an exterior surface of the electrically conductive measurement probe.

20. The method of claim 16, wherein the time rate of change in the capacitance of the capacitor is determined temporally adjacent the termination of the light pulse.

* * * * *

UNITED STATES PATENT AND TRADEMARK OFFICE
CERTIFICATE OF CORRECTION

PATENT NO. : 6,836,139 B2  Page 1 of 1
APPLICATION NO. : 10/277689
DATED : December 28, 2004
INVENTOR(S) : Howland It is certified that error appears in the above-identified patent and that said Letters Patent is hereby corrected as shown below:

<u>Face of the Patent</u>, See Item (73) Assignee: "Solid State Measurments, Inc." should read -- Solid State Measurements, Inc. --

Signed and Sealed this

Twenty-sixth Day of June, 2007

JON W. DUDAS
*Director of the United States Patent and Trademark Office*